(12) United States Patent
Yoshimura et al.

(10) Patent No.: US 7,638,652 B2
(45) Date of Patent: Dec. 29, 2009

(54) METHOD FOR PRODUCING FLUOROAMINE

(75) Inventors: Takafumi Yoshimura, Niigata (JP); Toshio Hidaka, Ibaraki (JP); Norio Fushimi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/373,583

(22) PCT Filed: Jul. 11, 2007

(86) PCT No.: PCT/JP2007/063810

§ 371 (c)(1), (2), (4) Date: Jan. 13, 2009

(87) PCT Pub. No.: WO2008/007696

PCT Pub. Date: Jan. 17, 2008

(65) Prior Publication Data

US 2009/0247789 A1    Oct. 1, 2009

(30) Foreign Application Priority Data

Jul. 13, 2006  (JP) .............................. 2006-192510

(51) Int. Cl.
    *C07C 209/50*  (2006.01)
(52) U.S. Cl. ........................ 564/412; 564/366; 564/414
(58) Field of Classification Search ........................ None
    See application file for complete search history.

(56) References Cited

U.S. PATENT DOCUMENTS

| 7,045,662 B2 | 5/2006 | Ebenbeck et al. |
| 2004/0198975 A1 | 10/2004 | Ebenbeck et al. |

FOREIGN PATENT DOCUMENTS

| JP | 2004-182665 | 7/2004 |
| JP | 2004-210792 | 7/2004 |
| WO | WO 03/002685 A1 | 1/2003 |
| WO | WO 2006/049014 A1 | 5/2006 |

OTHER PUBLICATIONS

Fawcett, F. S. et al., "Organic and Biological Chemistry", J. Amer. Chem. Soc., vol. 84, pp. 4275-4285 (Nov. 1962).

*Primary Examiner*—Brian J Davis
(74) *Attorney, Agent, or Firm*—Antonelli, Terry, Stout & Kraus, LLP.

(57) ABSTRACT

Provided is a one-step efficient production method for an α,α-difluoroamine of a general formula (1) below from an amide compound. The method is an economical method capable of producing the intended α,α-difluoroamine at high yield by reacting a starting amide compound with carbonyl fluoride and/or oxalyl fluoride under a specific condition.

Formula (1)

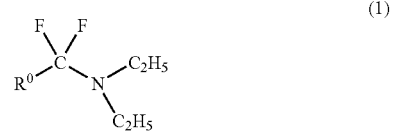

(1)

4 Claims, No Drawings

METHOD FOR PRODUCING FLUOROAMINE

This application is a 371 of PCT/JP2007/063810 filed Jul. 11, 2007.

TECHNICAL FIELD

The present invention relates to an efficient and excellent production method for a fluoroamine of a general formula (1). The α,α-difluoroamine of the general formula (1) is a nucleophilic fluorinating agent useful in production of medicines, etc.

[Formula 1]

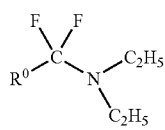

(wherein $R^0$ represents 2-methoxyphenyl or 3-methylphenyl).

BACKGROUND ART

The fluoroamine of the general formula (1) is a nucleophilic fluorinating agent having good thermal stability and excellent in handlability, and its typical compounds include N,N-diethyl-α,α-difluoro-(3-methylbenzyl)amine and N,N-diethyl-α,α-difluoro-(2-methoxybenzyl)amine (for example, see Patent References 2 and 3).

These compounds can selectively fluorinate a functional group such as an oxygen-containing functional group, a sulfur-containing functional group and a halogen group, and is greatly useful in production of functional chemicals such as medicines.

Heretofore, for obtaining these compounds, employed is a method of using the corresponding amide compound, an N,N-disubstituted amide of a formula (2) as the starting material, once reacting it with a halogenating agent that contains any other than fluorine, for example, chlorine, to produce the amide halide compound, and then reacting it with hydrogen fluoride or an alkali metal fluoride for interhalogenation.

[Formula 2]

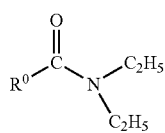

(wherein $R^0$ represents 2-methoxyphenyl or 3-methylphenyl).

Concretely, the oxygen atom on the amide bond of the compound of the formula (2) is substituted with chlorine atoms, using a chlorinating agent such as phosgene, phosphorus trichloride, phosphorus pentachloride, thionyl chloride, oxalyl chloride or the like, and the resulting amide chloride compound of a formula (3) is processed according to a known interhalogenation method with an alkali metal fluoride such as sodium fluoride or potassium fluoride, thereby giving the intended fluorine compound (for example, see Non-Patent References 1, 2, 3, 4).

[Formula 3]

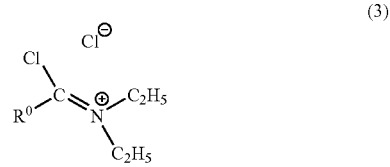

(wherein $R^0$ represents 2-methoxyphenyl or 3-methylphenyl).

The interhalogenation method can produce the intended product at a relatively good yield, but still has room for the improvement in point of the efficiency thereof in that the method requires two-stage reaction from the starting material to the product, and in addition, takes a long time for the 2nd-stage reaction of interhalogenation with potassium fluoride or the like; and therefore the method is not satisfactory as an industrial production method.

As opposed to this, reported is a method of producing an α,α-difluoroamine in one stage by fluorinating a starting material, N,N-disubstituted amide with carbonyl fluoride or oxalyl fluoride (for example, see Patent Reference 1, Non-Patent Reference 5). However, regarding the method of producing a fluoroamine of the formula (1) from an N,N-disubstituted amide of the formula (2), only an example of difluorinating a starting material, N,N-disubstituted amide at a reaction temperature of 50° C. is shown in Non-Patent Reference 5, and its yield is around 40% and is low. The present inventors tried producing N,N-diethyl-α,α-difluoro-(3-methylbenzyl)amine and N,N-diethyl-α,α-difluoro-(2-methoxybenzyl)amine from starting materials, N-N-diethyl-metatolamide and N,N-diethyl-(2-methoxy)benzamide, according to the reaction condition shown in these references, but the yield of the corresponding α,α-difluoroamine was extremely low.

Specifically, it has become clear that in order to produce a fluoroamine compound of the formula (1) in one-stage reaction, it is necessary to find out and establish a novel reaction condition for using an N,N-disubstituted amide of the formula (2) as the starting material.

[Patent Reference 1] JP-A 2004-210792
[Patent Reference 2] WO03/02685
[Patent Reference 3] JP-A 2004-182665
[Non-Patent Reference 1] B. Haveaux, A. Dekoker, M. Rens, A. R. Sidani, J. Toye, and L. Ghosez; Organic Synthesis, CV 6, 282
[Non-Patent Reference 2] G. A. Olah, J. T. Welch, Y. D. Vankar, M. Nojima, I. Kerekes, J. A. Olah; J. Org. Chem., 44, 3872 (1979)
[Non-Patent Reference 3] Y. Kimura; the Journal of the Society of Organic Synthetic Chemistry of Japan., 47, 258 (1989)
[Non-Patent Reference 4] Y. Yoshida, Y. Kimura; J. Fluorine. Chem., 44, 291 (1989)
[Non-Patent Reference 5] Fawcett, F. S. et al.; J. Amer. Chem. Soc., 84, 4275 (1962)

DISCLOSURE OF THE INVENTION

Problems that the Invention is to Solve

An object of the present invention is to provide an efficient and industrially-practicable production method for an α,α-difluoroamine of the formula (1), a nucleophilic fluorinating agent having good thermal stability and excellent in handlability.

Means for Solving the Problems

In view of the above-mentioned object, the present inventors have assiduously studied for the purpose of establishing a one-stage production method for an α,α-difluoroamine of the formula (1), and have found that the intended substance could not almost be obtained under the reaction condition described in the prior-art references, but unexpectedly, the intended substance can be produced at a high yield when a seemingly severe reaction condition is employed, and have completed the present invention.

Specifically, the present invention relates to a production method of the following 1 to 3, in which a fluoroamine of the formula (1) can be produced efficiently in one stage from an N,N-disubstituted amide of the formula (2).

[1] A method for producing a fluoroamine of a formula (1), comprising reacting an N,N-disubstituted amide of a formula (2) with carbonyl fluoride and/or oxalyl fluoride at a temperature of from 130 to 200° C. in the presence or absence of a solvent:

[Formula 4]

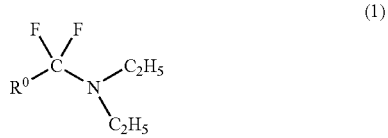

[Formula 5]

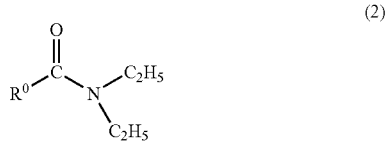

(wherein $R^0$ represents 2-methoxyphenyl or 3-methylphenyl);

[2] The method for producing a fluoroamine of the above 1, wherein the compound of the formula (2) is reacted with from 1.5 to 3.0 molar times, relative to the compound of the formula (2), of carbonyl fluoride and/or oxalyl fluoride;

[3] The method for producing a fluoroamine of the above 1 or 2, wherein the compound of the formula (2) is reacted with from to 2.5 molar times, relative to the compound of the formula (2), of carbonyl fluoride and/or oxalyl fluoride, at a temperature of from 140 to 180° C. in the presence or absence of a solvent.

EFFECT OF THE INVENTION

Heretofore, the production of an α,α-difluoroamine of the formula (1), a nucleophilic fluorinating agent having good thermal stability and excellent in handlability requires two-stage reaction of halogenation of an amide compound and subsequent interhalogenation; however, relative to the production, the present invention has made it possible to efficiently produce the intended product in one-stage reaction directly from the amide compound. Specifically, according to the present invention, an α,α-difluoroamine of the formula (1), a nucleophilic fluorinating agent having good thermal stability and excellent in handlability and useful in production of functional chemicals such as medicines, can be produced efficiently within a short period of time.

The production method for fluoroamine of the present invention is efficient in mass-production of the intended product, and is suitable for industrial-scale production thereof. The fluoroamine of the present invention is a nucleophilic fluorinating agent having good thermal stability and excellent in handlability and useful in production of functional chemicals such as medicines.

BEST MODE FOR CARRYING OUT THE INVENTION

Best modes for carrying out the present invention are described below.

In the compounds of the formulae (1) and (2), $R^0$ represents 2-methoxyphenyl or 3-methylphenyl.

In the reaction of an N,N-disubstituted amide of the formula (2) with carbonyl fluoride and/or oxalyl fluoride, the amount of carbonyl fluoride and/or oxalyl fluoride is from 1.5 to 3.0 molar times relative to the starting compound of the formula (2).

Even though the amount is less than 1.5 molar times, the intended product can be obtained, but the yield thereof is low and the method is inefficient as an industrial-scale process.

When the amount is more than 3.0 molar times, its does not have any negative influence on the reaction, but the reaction results could not be remarkably improved. The reaction temperature must be at least 130° C.; and when it is lower than 130° C., the reaction yield greatly lowers. On the other hand, the uppermost limit of the reaction temperature is limited by the decomposition temperature of the product, or that is, it is limited to be at most 200° C. More preferably, the amount of carbonyl fluoride and/or oxalyl fluoride to be used is from 1.7 to 2.5 molar times relative to the starting amide compound, and the reaction temperature is within a range of from 140 to 180° C.; and even more preferably, both the two conditions are satisfied.

The reaction in the present invention may be attained in any case in the presence or absence of a solvent. The usable organic solvent is not specifically defined, and may be anyone inert to the starting material and to the product. It includes aliphatic or aromatic hydrocarbons such as benzene, toluene, xylene, hexane, heptane, cyclohexane; and halogenohydrocarbons such as chlorobenzene, dichlorobenzene, carbon tetrachloride, chloroform, dichloromethane, dichloroethane; or their mixtures.

The reaction may be effected in any mode of batchwise or semi-batchwise reaction; however, the reaction is attained under heat, and a pressure reactor such as an autoclave must be used. After the reaction, the inside of the reactor is under pressure, as containing unreacted carbonyl fluoride and/or oxalyl fluoride as well as carbon dioxide. The unreacted carbonyl fluoride and/or oxalyl fluoride and carbon dioxide may be recovered and removed by degassing the container. In case where carbonyl fluoride and/or oxalyl fluoride still remaining in the reaction liquid must be removed, they may be recovered according to a suitable method of, for example, blowing an inert gas thereinto.

The reaction liquid from which the unreacted carbonyl fluoride and/or oxalyl fluoride are removed may be used as a nucleophilic fluorinating agent directly as it is, but by processing for distillation, this may be a fluorinating agent having a further higher purity. The fluorinating agent for use in the invention may readily react with water and decompose, and therefore it is desirable that all the operation relating to reaction, purification, storage and shipment is effected in a dry inert atmosphere.

EXAMPLES

The method for producing a fluoroamine of the present invention is described concretely with reference to the following Examples. The present invention should not be limited to the embodiments of the following Examples. The compounds in the Examples are analyzed according to the method mentioned below.

NMR Determination

Using JEOL's NMR-LA500SS (500 MHz), the sample is analyzed in a heavy chloroform solvent.

Example 1

Production of N,N-diethyl-α,α-difluoro-(3-methyl)benzylamine

A starting amide compound, N,N-diethyl-metatolamide (19.11 g, 0.1 mol) was put into an autoclave (300 ml), closed and purged with nitrogen. Using a vacuum pump, the autoclave was degassed, and carbonyl fluoride (12.3 g, 0.186 mol) was put into it. With stirring, the contents were heated at 170° C. with a heater, and reacted at that temperature for 10 hours.

After the reaction, the heating was stopped, the pressure in the reactor was reduced, and the unreacted carbonyl fluoride was absorbed by water with ice. In nitrogen, the contents were taken out from the bottom of the reactor and transferred into a flask, the flask was heated at about 60° C., and the unreacted carbonyl fluoride was removed under reduced pressure. The product was analyzed for NMR resulting in that the reaction yield of N,N-diethyl-α,α-difluoro-(3-methyl)benzylamine was 66%. The product was subjected to distillation under reduced pressure (55 to 57° C./4 mmHg), thereby giving an isolated pure substance, N,N-diethyl-α,α-difluoro-(3-methyl)benzylamine (11.97 g, isolation yield 56%). The pure product was analyzed for NMR, resulting in that its purity was 100%. The yield is based on N,N-diethyl-metatolamide (Table 1).

(NMR Data)

$^1$H-NMR: δ (ppm), TMS standard, in CDCl$_3$, 1.02 (t, 6H, —CH$_3$×2), 2.33 (s, 3H, —CH$_3$), 12.84 (q, 4H, —CH$_2$-×2). $^{13}$C-NMR: 5 (ppm), TMS standard, in CDCl$_3$, at −50° C., 13.7 (s, —CH$_3$×2), 21.2 (s, —CH$_3$), 40.0 (s, —CH$_2$-×2), 123.7, 127.1, 128.0, 130.6, 137.9 (s, aromatic ring: —CH-×2), 136.2 (t, 32 Hz, —CF$_2$).

19 F-NMR: δ (ppm), CF$_3$COOH base, in CDCl$_3$, at −50° C., −73.7 (s, =CF$_2$).

Example 2

Production of N,N-diethyl-α,α-difluoro-(2-methoxy)benzylamine

A starting amide compound, N,N-diethyl-(2-methoxy)benzamide was processed in the same manner as in Example 1, except that its amount used was changed to 20.78 g (0.1 mol). The product was analyzed for NMR resulting in that the reaction yield of N,N-diethyl-α,α-difluoro-(2-methoxy)benzylamine was 65. The product was subjected to distillation under reduced pressure (77 to 80° C./2 mmHg), thereby giving an isolated pure substance, N,N-diethyl-α,α-difluoro-(2-methoxy)benzylamine (12.6 g isolation yield 55%). The pure product was analyzed for NMR, resulting in that its purity was 100%.

The yield is based on N,N-diethyl-(2-methoxy)benzamide (Table 1).

(NMR Data)

H-NMR: δ (ppm), TMS standard, in CDCl$_3$, 1.03 (t, 6H, —CH$_3$×2), 3.28 (s, 3H, —OCH$_3$), 2.92 (q, 4H, —CH$_2$-×2). $^{13}$C-NMR: δ (ppm), TMS standard, in CDCl$_3$, at −50° C., 13.65 (S, —CH$_3$×2), 55.75 (s, —OCH$_3$), 39.69 (s, —CH$_2$-×2), 112.02, 119.93, 128.60, 131.46, 157.26 (s, aromatic ring: —CH-×5), 122.8 (br, —CF$_2$). $^{19}$F-NMR: δ (ppm), CF$_3$COOH base, in CDCl$_3$, at −50° C., −68.35 (s, =CF$_2$).

Example 3

Production of N,N-diethyl-α,α-difluoro-(3-methyl)benzylamine

The same process as in Example 1 was carried out, in which, however, the amount of carbonyl fluoride was changed to 16.5 g (0.25 mol) and the reaction temperature was to 155° C. The product was analyzed for NMR, resulting in that the reaction yield of N,N-diethyl-α,α-difluoro-(3-methyl)benzylamine was 62% (Table 1).

Example 4

Production of N,N-diethyl-α,α-difluoro-(3-methyl)benzylamine

The same process as in Example 1 was carried out, in which, however, the amount of carbonyl fluoride was changed to 12.5 g (0.19 mol), dichloroethane (50 g) was used as a solvent, and the reaction temperature was changed to 158° C. The product was analyzed for NMR, resulting in that the reaction yield of N,N-diethyl-α,α-difluoro-(3-methyl)benzylamine was 60% (Table 1).

Comparative Example 1

Production of N,N-diethyl-α,α-difluoro-(3-methyl)benzylamine

The same process as in Example 1 was carried out, in which, however, the amount of carbonyl fluoride was changed to 12.2 g (0.184 mol) and the reaction temperature was to 120° C. The product was analyzed for NMR, resulting in that the reaction yield of N,N-diethyl-α,α-difluoro-(3-methyl)benzylamine was only 20% (Table 1).

Comparative Example 2

Production of N,N-diethyl-α,α-difluoro-(2-methoxy)benzylamine

The same process as in Example 1 was carried out, in which, however, the amount of N,N-diethyl-(2-methoxy)benzamide was changed to 20.78 g (0.1 mol), the amount of oxalyl fluoride was 14.5 g (0.186 mol) and the reaction temperature was changed to 100° C. The product was analyzed for NMR, resulting in that the reaction yield of N,N-diethyl-α,α-difluoro-(2-methoxy)benzylamine was only 11% (Table 1).

Comparative Example 3

Production of N,N-diethyl-α,α-difluoro-(3-methyl)benzylamine

The same process as in Example 1 was carried out, in which, however, the amount of N,N-diethyl-metatolamide was changed to 38.51 g (0.2 mol), the amount of carbonyl fluoride was to 17.7 g (0.268 mol) and the reaction temperature was to 72° C. The product was analyzed for NMR, resulting in that the reaction yield of N,N-diethyl-α,α-difluoro-(3-methyl)benzylamine was only 7% (Table 1).

Comparative Example 4

Production of N,N-diethyl-α,α-difluoro-(3-methyl)benzylamine

The same process as in Example 1 was carried out, in which, however, the amount of carbonyl fluoride was changed to 7.0 g (0.106 mol). dichloromethane (62 g) was used as a solvent, and the reaction temperature was changed to 50° C. The product was analyzed for NMR, but the intended substance could not be detected (Table 1).

TABLE 1

|  | Reaction Temperature (° C.) | Fluorinating Agent/ N,N-disubstituted amide (ratio by mol) | Reaction Yield (%) | Isolation Yield (%) |
| --- | --- | --- | --- | --- |
| Example 1 | 170 | 1.9 | 66 | 56 |
| Example 2 | 170 | 1.0 | 65 | 55 |
| Example 3 | 155 | 2.5 | 62 |  |
| Example 4 | 158 | 1.9 | 60 |  |
| Comparative Example 1 | 120 | 1.8 | 20 |  |
| Comparative Example 2 | 100 | 1.9 | 11 |  |
| Comparative Example 3 | 72 | 1.3 | 7 |  |
| Comparative Example 4 | 50 | 1.1 | 0 |  |

INDUSTRIAL APPLICABILITY

According to the production method for fluoroamine of the present invention, the intended product, N,N-diethyl-α,α-difluoro-(3-methylbenzyl)amine or N,N-diethyl-α,α-difluoro-(2-methoxybenzyl)amine can be produced efficiently in one-step reaction from a starting amide compound. The nucleophilic fluorinating agent, α,α-difluoroamine is efficiently utilized for production of functional chemical such as medicines.

The invention claimed is:

1. A method for producing a fluoroamine of a formula (1), comprising reacting an N,N-disubstituted amide of a formula (2) with carbonyl fluoride and/or oxalyl fluoride at a temperature of from 130 to 200° C. in the presence or absence of a solvent:

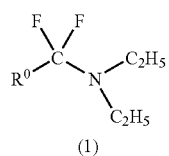

[Formula 1]

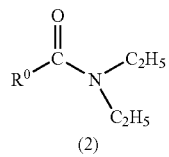

[Formula 2]

(wherein $R^0$ represents 2-methoxyphenyl or 3-methylphenyl).

2. The method for producing a fluoroamine as claimed in claim 1, wherein the compound of the formula (2) is reacted with from 1.5 to 3.0 molar times, relative to the compound of the formula (2), of carbonyl fluoride and/or oxalyl fluoride.

3. The method for producing a fluoroamine as claimed in claim 1, wherein the compound of the formula (2) is reacted with from 1.7 to 2.5 molar times, relative to the compound of the formula (2), of carbonyl fluoride and/or oxalyl fluoride, at a temperature of from 140 to 180° C. in the presence or absence of a solvent.

4. The method for producing a fluoroamine as claimed in claim 2, wherein the compound of the formula (2) is reacted with from 1.7 to 2.5 molar times, relative to the compound of the formula (2), of carbonyl fluoride and/or oxalyl fluoride, at a temperature of from 140 to 180° C. in the presence or absence of a solvent.

* * * * *